(12) United States Patent
Deslauriers et al.

(10) Patent No.: US 6,848,537 B2
(45) Date of Patent: Feb. 1, 2005

(54) STETHOSCOPE

(76) Inventors: Richard J. Deslauriers, 87 Carmel Hill Rd., Woodbury, CT (US) 06798; Robert T. Potash, 20 Pondunk Cir., S. Windsor, CT (US) 06074

( * ) Notice: Subject to any disclaimer, the term of this patent is extended or adjusted under 35 U.S.C. 154(b) by 342 days.

(21) Appl. No.: 09/908,557

(22) Filed: Jul. 20, 2001

(65) Prior Publication Data
US 2001/0042656 A1 Nov. 22, 2001

Related U.S. Application Data

(63) Continuation-in-part of application No. 09/557,764, filed on Apr. 25, 2000.
(51) Int. Cl.[7] .................................................. A61B 7/02
(52) U.S. Cl. ....................................... 181/131; 181/137
(58) Field of Search .................................. 181/131, 137

(56) References Cited

U.S. PATENT DOCUMENTS 5,530,212 A    6/1996  Baffoni
5,774,563 A    6/1998  DesLauriers et al.

Primary Examiner—Khanh Dang

(57) ABSTRACT

A stethoscope is described. The stethoscope includes a head assembly, an ear piece assembly, and a tubing assembly. The tubing assembly has a first end connected to the head assembly and a second end connected to the ear piece assembly. The tubing assembly includes a first acoustic chamber and three insulation chambers. The insulation chambers include a first material having a first density and are disposed around the first acoustic chamber. The tubing assembly also includes an outer layer, which includes a second material having a second density. Moreover, the outer layer is disposed around the insulation chambers. In another embodiment, the outer layer is substantially frictionless and the tubing assembly is flexible. In yet another embodiment, the stethoscope further includes a second acoustic chamber and the insulation chambers are disposed around a portion of the first acoustic chamber and a portion of the second acoustic chamber.

62 Claims, 4 Drawing Sheets

STETHOSCOPE

The present application is continuation in part of U.S. patent application Ser. No. 09/557,764, entitled "Improved Acoustic Conduit for use with a Stethoscope," which was filed on Apr. 25, 2000, the disclosure of which is incorporated herein by reference, in its entirety.

BACKGROUND OF THE INVENTION

1. Field of the Invention

The present invention relates generally to the field of stethoscopes. In particular, the present invention relates to an acoustic conduit or tube of a stethoscope.

2. Description of Related Art

Auscultation may be used to diagnosis medical ailments. Stethoscopes may allow a healthcare provider to listen to and identify sounds, and these sounds may be associated with various abnormalities or ailments. One such sound is a heart murmur, which, when detected, may indicate that a patient possesses a specific abnormality of the heart. Identifying the specific sound indicative of the specific heart murmur may be difficult.

Some known stethoscopes are designed to detect sounds produced in a human body. One known stethoscope includes a plurality of ear pieces connected to a bell/diaphragm by a tube for receiving sounds. This known stethoscope may be useful in detecting some sounds associated with specific abnormalities. However, may physiological sounds are reproduced without sufficient clarity to perform rapid and accurate diagnosis when using this known stethoscope. Further, artifact from external noise may distort physiological sounds, such that it may be difficult to detect some sounds associated with specific abnormalities using this known stethoscope.

One factor which may affect the quality of sound reproduced by a stethoscope is a stethoscope head and an acoustic conduit or tube. In one known stethoscope, the acoustic conduit may be a single acoustic chamber formed by the inner diameter of a flexible hollow tube or, alternatively, by two acoustic chambers attached side by side, so as to maintain individual conduits for each ear piece. However, this known stethoscope may be susceptible to artifact interference from external noise caused by indirect and direct contact with the acoustic conduit(s).

SUMMARY OF THE INVENTION

Therefore a need has arisen for a stethoscope that overcomes these and other shortcomings of the related art. A technical advantage of the present invention is that the acoustic conduit may reduce external noise interference. Another technical advantage of the present invention is that the acoustic conduit may have a flexible interface. Yet another technical advantage of the present invention is that an outer surface of the acoustic conduit may be substantially frictionless, which may dampen external noise which enters the acoustic chamber.

In an embodiment of the present invention, a stethoscope is described. The stethoscope comprises a head assembly, an ear piece assembly, and a tubing assembly. The tubing assembly has a first end connected to the head assembly and a second end connected to the ear piece assembly. The tubing assembly comprising a first acoustic chamber and at least one insulation chamber. The at least one insulation chamber comprises a first material having a first density, in which at least a portion of the at least one insulation chamber is disposed around at least a portion of the first acoustic chamber. The tubing assembly further comprises an outer layer, which comprises a second material having a second density. Moreover, the outer layer is disposed around the at least one insulation chamber. In another embodiment, the outer layer is substantially frictionless and the tubing assembly is flexible. In yet another embodiment, the stethoscope further comprises a second acoustic chamber and at least a portion of the at least one insulation chamber is disposed around at least a portion of the second acoustic chamber.

In another embodiment of the present invention, a stethoscope is described. The stethoscope comprises a head assembly, an ear piece assembly, and a tubing assembly. The tubing assembly has a first end connected to the head assembly and a second end connected to the ear piece assembly. The tubing assembly comprises a first acoustic chamber and an outer layer, in which the outer layer forms an enclosure around the first acoustic chamber. Moreover, the exterior surface of the outer layer has a roughness peak count greater than about 45 peaks per cm.

In still a further embodiment of the present invention, A tubing assembly is described. The tubing assembly comprises a first acoustic chamber and at least one insulation chamber. The insulation chamber also comprises a first material having a first density, in which at least a portion of the at least one insulation chamber is disposed around at least a portion of the first acoustic chamber. The tubing assembly further comprises an outer layer, which comprises a second material having a second density, in which the outer layer is disposed around the at least one insulation chamber.

Other objects, features, and advantages will be apparent to persons of ordinary skill in the art in view of the following detailed description of the invention and the accompanying drawings.

BRIEF DESCRIPTION OF THE DRAWINGS

For a more complete understanding of the present invention, the needs satisfied thereby, and the features and advantages thereof, reference now is made to the following descriptions taken in connection with the accompanying drawings.

DETAILED DESCRIPTION OF PREFERRED EMBODIMENTS

Preferred embodiments of the present invention and their advantages may be understood by referring to FIGS. 1–5, like numerals being used for like corresponding parts in the various drawings.

Figure 1A:
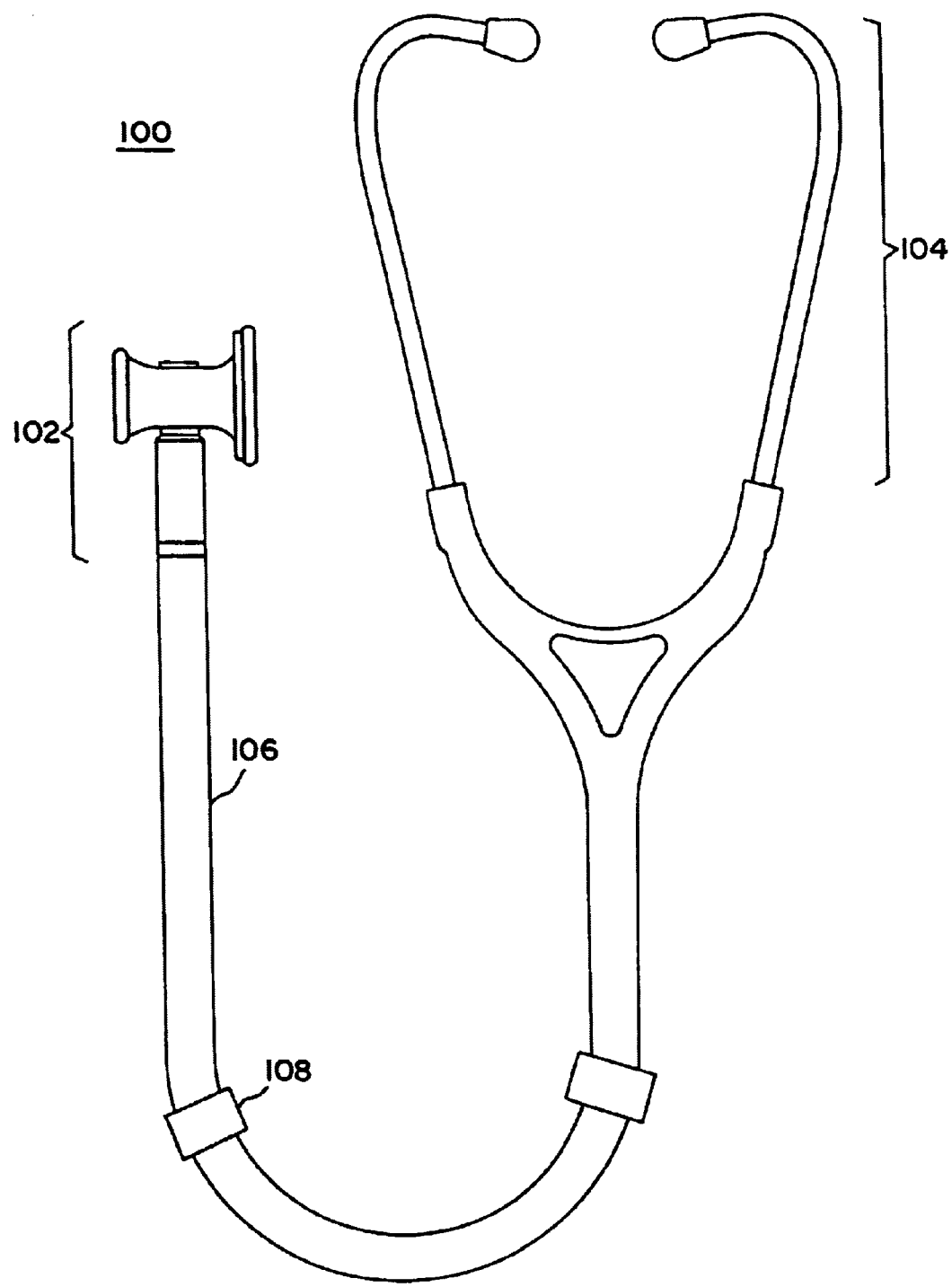
FIG. 1a is a perspective view of a stethoscope according to an embodiment of the present invention.

Referring to FIG. 1a, a stethoscope 100 according to an embodiment of the present invention is described. Stethoscope 100 comprises a head assembly 102, which may be manufactured from a medical grade stainless steel, titanium, or the like, and an ear piece assembly 104. Stethoscope 100 also comprises a tubing assembly 106, which may have a first end connected to head assembly 104 and a second end connected to ear piece assembly 104.

Figure 1B:
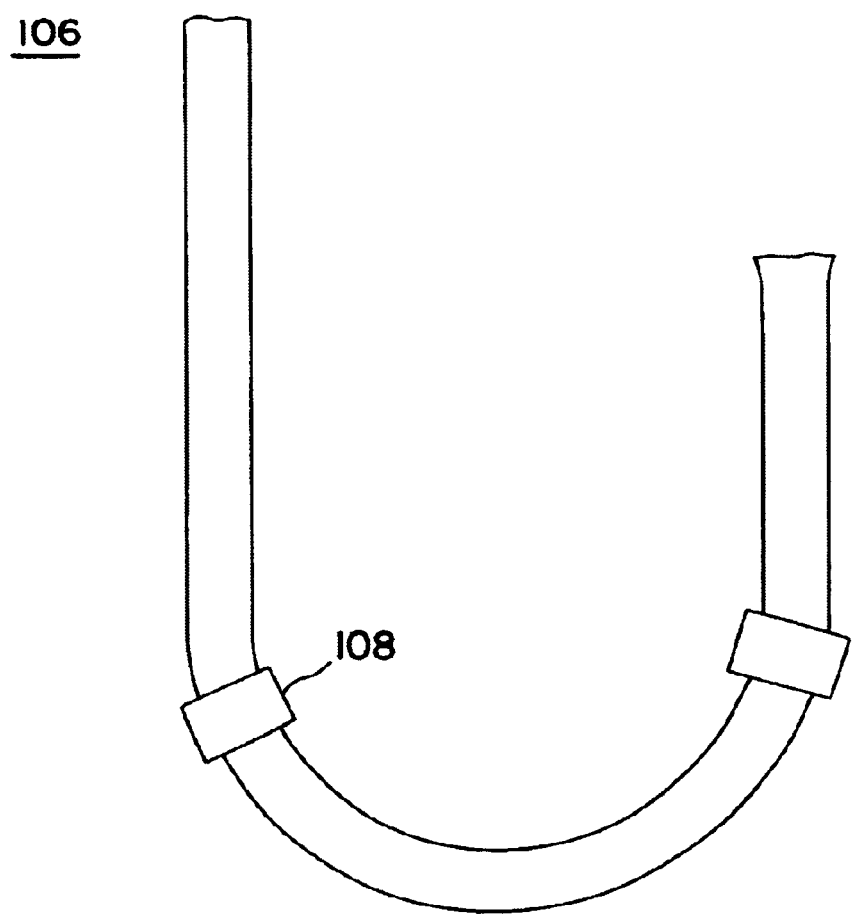
FIG. 1b is a perspective view of a tubing assembly according to an embodiment of the present invention.
Figure 2:
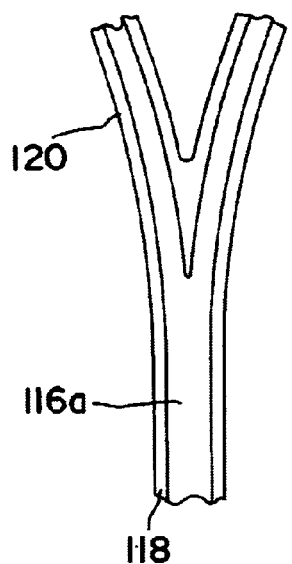
FIG. 2 is a cross-sectional view of a stethoscope tube according to an embodiment of the present invention.
Figure 3:
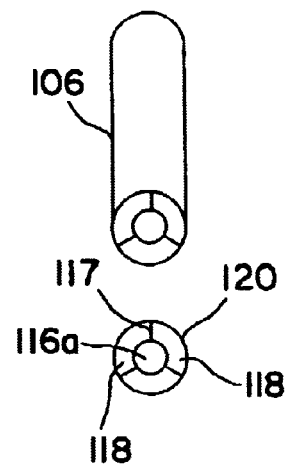
FIG. 3 is a cross-sectional view of a stethoscope tube according to another embodiment of the present invention.

Referring to FIGS. 1b, 2, and 3, tubing assembly 106 according to an embodiment of the present invention is described. It will be understood by those of ordinary skill in the art that tubing assembly 106 may be employed with stethoscope 100, or alternatively, may be a separate assembly employable with a sound carrying apparatus other than a stethoscope. Tubing assembly 106 may comprise a first acoustic chamber 116a. Acoustic chamber 116a may be flexible, or alternatively, may be substantially non-flexible. Acoustic chamber 116a may comprise a tube, such as a rubber tube, and further may comprise at least one coiled element disposed within acoustic chamber 116a. For example, the coiled element may be a spring, compression spring, or the like. In one embodiment, the spring may be a stainless steel spring.

Tubing assembly 106 also may comprise at least one filter chamber or insulation chamber 118. Insulation chamber 118 may substantially reduce an amount of external noise entering acoustic chamber 116a. In one embodiment, a number of insulation chambers 118 may be three. In an embodiment in which the number of insulation chambers is greater than one, an insulation chamber end wall 117 may be formed between each of the individual insulation chambers 118. End wall 117 may support the individual acoustic chambers 118 and also may prevent a collapsing of insulation chambers 118. In each of the above described embodiments, at least a portion of insulation chamber 118 may be disposed around at least a portion of acoustic chamber 116a, such that at least a portion of insulation chamber 118 may be molded to least a portion of the external surface of acoustic chamber 116a. Insulation chamber 118 may comprise a coiled or flexible element disposed within insulation chamber 118, such as a spring, compression spring, or the like. The coiled or flexible element may act as a mandrel and as a heat sink during the molding of insulation chamber 118 to the external surface of acoustic chamber 116a. Insulation chamber 118 also may decrease an amount of external noise which may enter acoustic chamber 116a. Moreover, insulation chamber 118 may be manufactured from a first material having a first density, such as stainless steel or another metal.

Tubing assembly 106 also may comprise an outer layer 120. For example, outer layer 120 may be a tube, or, alternatively, may be a sheath. Outer layer 120 may be disposed around insulation chamber 118, such that outer layer 120 may be in direct contact with insulation chamber 118, but may not be in direct contact with acoustic chamber 116a. Moreover, outer layer 120 may be flexible, and also may be manufactured from a second material having a second density, such as Neoprene, chlorinated Neoprene, or the like. Alternatively, the second material may be a polymer, such as silicon, a latex, a PVC tube or a rubber material.

In one embodiment of the present invention, the first density may be greater than the second density, such that insulation chamber 118 may be more dense than outer layer 120. Alternatively, the second density may be greater than the first density, such that outer layer 120 may be more dense than insulation chamber 118. Either of these density mismatches between insulation chamber 118 and outer layer 120 also may result in an impedance mismatch between insulation chamber 118 and outer layer 120. This impedance mismatch may decrease the amount of external noise which may enter acoustic chamber 116a. In another embodiment, insulation chamber 118 further may comprise a fluid, such as water or another liquid which may result in an impedance mismatch between insulation chamber 118 and outer layer 120, which may be disposed within insulation chamber 118. Alternatively, insulation chamber 118 further may comprise a gas, such as air or another gas which may result in an impedance mismatch between insulation chamber 118 and outer layer 120, which may be disposed within insulation chamber 118. In another embodiment, insulation chamber 118 further may comprise a a displaceable solid, such as a foam or another low density displaceable solid, which may result in an impedance mismatch between insulation chamber 118 and outer layer 120, which may be disposed within insulation chamber 118. Filling at least a portion of insulation chamber 118 with a gas, liquid, displaceable solid, or combinations thereof, further may decrease the amount of external noise which may enter acoustic chamber 116a. In still a further embodiment of the present invention, insulation chamber 118 may comprise at least one insulation layer disposed within insulation chamber 118. The at least one insulation layer may substantially fill insulation chamber 118, or alternatively, may fill only a portion of insulation chamber 118.

In yet another embodiment of the present invention, an external surface of outer layer 120 also may be coated with a third material, which may be a chemical. For example, the external surface of outer layer 120 may be coated with polytetra-fluoroethlene. Alternatively, the external surface of outer layer 120 may be coated another known material, such that the roughness peak count of the external surface may be increased. The roughness peak count of a surface may measure the peak density of the material on the surface. Moreover, as the roughness peak count increases, the surface friction may decrease. For example, in one embodiment, the roughness peak count of the external surface may be greater than about 45 peaks per cm. Alternatively, the roughness peak count of the external surface may be between about 45 peaks per cm and about 100 peaks per cm, or may be substantially frictionless. In each of the above-described embodiments, tubing assembly 106 further may include anti-slip means, such as at least one anti-slip ring 108. Anti-slip ring 108 may be disposed around the external surface of outer layer 120 and may comprise rubber, grated rubber, or the like. Alternatively, anti-slip ring may comprise a material having a non-frictionless surface, such that stethoscope 100 may not readily slide off the neck of a user of stethoscope 100.

Figure 4:
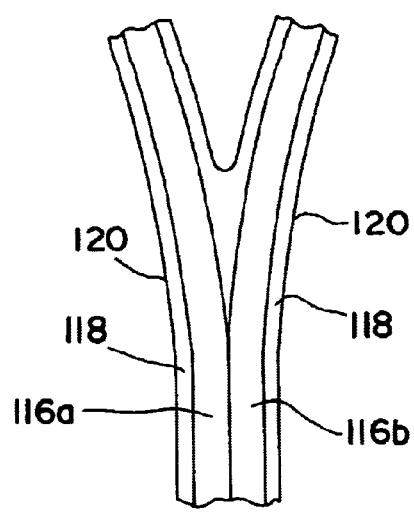
FIG. 4 is a cross-sectional view of a stethoscope tube according to yet another embodiment of the present invention.
Figure 5:
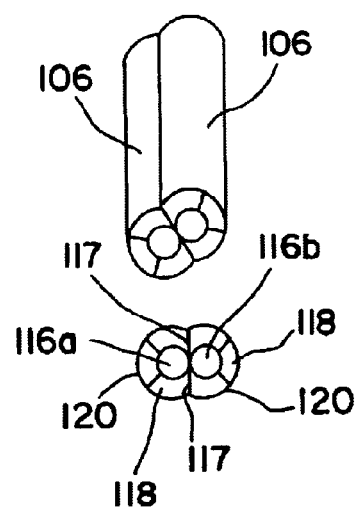
FIG. 5 is a cross-sectional view of a stethoscope tube according to still another embodiment of the present invention.

Referring to FIGS. 4 and 5, tubing assembly 106 according to another embodiment of the present invention is described. Tubing assembly 106 may comprise a first acoustic chamber 116a and a second acoustic chamber 116b. Acoustic chambers 116a and 116b may be flexible, or alternatively, may be substantially non-flexible. Acoustic chambers 116a and 116b may each comprise a tube, such as a rubber tube, and further may comprise at least one coiled element disposed within acoustic chambers 116a and 116b, respectively. The coiled element may be a spring, compression spring, or the like. In one embodiment, the spring may be a stainless steel spring.

Tubing assembly 106 also may comprise at least one filter chamber or insulation chamber 118. Insulation chamber 118 may substantially reduce an amount of external noise entering acoustic chambers 116a and 116b. In one embodiment, a number of insulation chambers 118 may be six. In an embodiment in which the number of insulation chambers is greater than one, an insulation chamber end wall 117 may be formed between each of the individual insulation chambers 118. End wall 117 may support the individual acoustic chambers 118 and also may prevent a collapsing of insulation chambers 118. In each of the above described embodiments, at least a portion of insulation chamber 118 may be disposed around at least a portion of acoustic chamber 116a, such that at least a portion of insulation chamber 118 may be molded to at least a portion of the external surface of acoustic chamber 116a. Similarly, at least a portion of insulation chamber 118 may be disposed around at least a portion of acoustic chamber 116a, such that at least a portion of insulation chamber 118 may be molded to at least a portion of the external surface of acoustic chamber 116a. Insulation chamber 118 may comprise a coiled or flexible element disposed within acoustic chamber 118, such as a spring, compression spring, or the like. The coiled or flexible element may act as a mandrel and as a heat sink during the molding of insulation chamber 118 to the external surfaces of acoustic chambers 116a and 116b, respectively. Insulation chamber 118 also may decrease an amount of external noise which may enter acoustic chambers 116a and 116, respectively. Moreover, insulation chamber 118 may be manufactured from a first material having a first density, such as stainless steel or another metal.

Tubing assembly 106 also may comprise an outer layer 120. For example, outer layer 120 may be a tube, or, alternatively, may be a sheath. Outer layer 120 may be disposed around insulation chamber 118, such that outer layer 120 may be in direct contact with insulation chamber 118, but may not be in direct contact with either acoustic chamber 116a or acoustic chamber 116b. Moreover, outer layer 120 may be flexible, and also may be manufactured from a second material having a second density, such as Neoprene, chlorinated Neoprene, or the like. Alternatively, the second material may be a polymer, such as silicon, a latex, a PVC tube, or a rubber material.

In one embodiment of the present invention, the first density may be greater than the second density, such that insulation chamber 118 may be more dense than outer layer 120. Alternatively, the second density may be greater than the first density, such that outer layer 120 may be more dense than insulation chamber 118. Either of these density mismatches between insulation chamber 118 and outer layer 120 also may result in an impedance mismatch between insulation chamber 118 and outer layer 120. This impedance mismatch may decrease the amount of external noise which may enter acoustic chamber 116a and 116b, respectively. In another embodiment, insulation chamber 118 further may comprise a fluid, such as water or another liquid which may result in an impedance mismatch between insulation chamber 118 and outer layer 120, which may be disposed within insulation chamber 118. Alternatively, insulation chamber 118 further may comprise a gas, such as air or another gas which may result in an impedance mismatch between insulation chamber 118 and outer layer 120, which may be disposed within insulation chamber 118. In another embodiment, insulation chamber 118 further may comprise a a displaceable solid, such as a foam or another low density displaceable solid, which may result in an impedance mismatch between insulation chamber 118 and outer layer 120, which may be disposed within insulation chamber 118. Filling at least a portion of insulation chamber 118 with a gas, liquid, displaceable solid, or combinations thereof, further may decrease the amount of external noise which may enter acoustic chamber 116a and 116b, respectively. In still a further embodiment of the present invention, insulation chamber 118 may comprise at least one insulation layer disposed within insulation chamber 118. The at least one insulation layer may substantially fill insulation chamber 118, or alternatively, may fill only a portion of insulation chamber 118.

In yet another embodiment of the present invention, an external surface of outer layer 120 also may be coated with a third material, which may be a chemical. For example, the external surface of outer layer 120 may be coated with polytetra-fluoroethlene. Alternatively, the external surface of outer layer 120 may be coated another known material, such that the roughness peak count of the external surface may be increased. The roughness peak count of a surface may measure the peak density of the material on the surface. Moreover, the as the roughness peak count increases, the surface friction may decrease. For example, in one embodiment, the roughness peak count of the external surface may be greater than about 45 peaks per cm. Alternatively, the roughness peak count of the external surface may be between about 45 peaks per cm and about 100 peaks per cm, or may be substantially frictionless. In each of the above-described embodiments, tubing assembly 106 further may include anti-slip means, such as at least one anti-slip ring 108. Anti-slip ring 108 may be disposed around the external surface of outer layer 120 and may comprise rubber, grated rubber, or the like. Alternatively, anti-slip ring may comprise a material having a non-frictionless surface, such that stethoscope 100 may not readily slide off the neck of a user of stethoscope 100.

While the invention has been described in connection with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein.

What is claimed is:

1. A stethoscope comprising:
    a head assembly;
    an ear piece assembly; and
    a tubing assembly having a first end connected to said head assembly and a second end connected to said ear piece assembly, said tubing assembly comprising:
        a first acoustic chamber;
        at least one insulation chamber comprising a first material having a first density, wherein at least a portion of said at least one insulation chamber is disposed around at least a portion of said first acoustic chamber;
        and an outer layer comprising a second material having a second density, wherein said outer layer is disposed around said at least one insulation chamber, and an exterior surface of said outer layer has a roughness peak count greater than about 45 peaks per cm.

2. The stethoscope of claim 1, wherein said first density is greater than said second density.

3. The stethoscope of claim 1, wherein at least a portion of said at least one insulation chamber is molded to at least a portion of the external surface of said first acoustic chamber.

4. The stethoscope of claim 1, wherein said first acoustic chamber and said outer layer do not touch.

5. The stethoscope of claim 1, wherein said second density is greater than said first density.

6. The stethoscope of claim 4, further comprising a second acoustic chamber, wherein at least a portion of said at least one insulation chamber is disposed around at least a portion of said second acoustic chamber.

7. The stethoscope of claim 6, wherein at least a portion of said at least one insulation chamber is molded to at least a portion of the external surface of said second acoustic chamber.

8. The stethoscope of claim 6, wherein said second acoustic chamber and said outer layer do not touch.

9. The stethoscope of claim 1, wherein said outer layer further comprises a third material, wherein the exterior surface of said outer layer is coated with said third material and is substantially frictionless.

10. The stethoscope of claim 9, wherein said third material comprises polytetra-fluoroethlene.

11. The stethoscope of claim 9, wherein said tubing assembly further comprises anti-slip rings disposed around said outer layer.

12. The stethoscope of claim 1, wherein said outer layer further comprises a third material, wherein the exterior surface of said outer layer is coated with said third material and said coated exterior surface of said outer layer has a roughness peak count greater than about 45 peaks per cm.

13. The stethoscope of claim 1, wherein said roughness peak count is between about 45 peaks per cm and about 100 peaks per cm.

14. The stethoscope of claim 9, wherein said third material is polytetra-fluoroethlene.

15. The stethoscope of claim 12, wherein said tubing assembly further comprises anti-slip rings disposed around said outer layer.

16. The stethoscope of claim 1, wherein said second material comprises a polymer or a rubber material.

17. The stethoscope of claim 1, wherein said second material comprises at least one material selected from the group consisting of Neoprene and chlorinated Neoprene.

18. The stethoscope of claim 1, wherein said first material comprises stainless steel.

19. The stethoscope of claim 1, wherein said at least one insulation chamber further comprises at least one first coiled element disposed within said at least one insulation chamber.

20. The stethoscope of claim 1, wherein said at least one first coiled element is a spring.

21. The stethoscope of claim 15, wherein said first acoustic chamber comprises at least one second coiled element disposed within said first acoustic chamber.

22. The stethoscope of claim 1, wherein said at least one insulation chamber further comprises at least one gas element disposed within said at least one insulation chamber.

23. The stethoscope of claim 1, wherein said at least one insulation chamber further comprises at least one liquid substance disposed within said at least one insulation chamber.

24. The stethoscope of claim 1, wherein said at least one insulation chamber further comprises at least one displaceable solid disposed within said at least one insulation chamber.

25. The stethoscope of claim 24, wherein said displaceable solid is foam.

26. The stethoscope of claim 1, wherein said insulation chamber comprises at least one insulation layer disposed within said insulation chamber.

27. The stethoscope of claim 26, wherein said at least one insulation layer substantially fills said insulation chamber.

28. A stethoscope comprising:
a head assembly;
an ear piece assembly; and
a tubing assembly having a first end connected to said head assembly and a second end connected to said ear piece assembly, said tubing assembly comprising:
a first acoustic chamber comprising at least one coiled element disposed within said first acoustic chamber;
at least one insulation chamber, wherein at least a portion of said at least one insulation chamber is disposed around at least a portion of said first acoustic chamber;
and an outer layer, wherein said outer layer is disposed around said at least one insulation chamber, and an exterior surface of said outer layer has a roughness peak count greater than about 45 peaks per cm.

29. A stethoscope comprising:
a head assembly;
an ear piece assembly; and
a tubing assembly having a first end connected to said head assembly and a second end connected to said ear piece assembly, said tubing assembly comprising:
a first acoustic chamber; and
and an outer layer, wherein said outer layer forms an enclosure around said first acoustic chamber and the exterior surface of said outer layer has a roughness peak count greater than about 45 peaks per cm.

30. The stethoscope of claim 29, wherein said tubing assembly further comprises anti-slip rings disposed around said outer layer.

31. The stethoscope of claim 29, wherein said exterior surface of said outer layer is coated with at least one first material.

32. The stethoscope of claim 31, wherein said first material comprises polytetra-fluoroethlene.

33. The stethoscope of claim 29, wherein said roughness peak count is between about 45 peaks per cm and about 100 peaks per cm.

34. The stethoscope of claim 33, wherein said tubing assembly further comprises at least one insulation chamber, wherein at least a portion of said at least one insulation chamber is disposed between at least a portion of said first acoustic chamber and said outer layer.

35. A tubing assembly comprising:
a first acoustic chamber;
at least one insulation chamber comprising a first material having a first density, wherein at least a portion of said at least one insulation chamber is disposed around at least a portion of said first acoustic chamber;
and an outer layer comprising a second material having a second density, wherein said outer layer is disposed around said at least one insulation chamber, and an exterior surface of said outer layer has a roughness peak count greater than about 45 peaks per cm.

36. The tubing assembly of claim 35, wherein said first density is greater than said second density.

37. The tubing assembly of claim 35, wherein at least a portion of said at least one insulation chamber is molded to at least a portion of the external surface of said first acoustic chamber.

38. The tubing assembly of claim 35, wherein said first acoustic chamber and said outer layer do not touch.

39. The tubing assembly of claim 35, wherein said second density is greater than said first density.

40. The tubing assembly of claim 38, further comprising a second acoustic chamber, wherein at least a portion of said at least one insulation chamber is disposed around at least a portion of said second acoustic chamber.

41. The tubing assembly of claim 40, wherein at least a portion of said at least one insulation chamber is molded to at least a portion of the external surface of said second acoustic chamber.

42. The tubing assembly of claim 40, wherein said second acoustic chamber and said outer layer do not touch.

43. The tubing assembly of claim 35, wherein said outer layer further comprises a third material, wherein the exterior surface of said outer layer is coated with said third material and is substantially frictionless.

44. The tubing assembly of claim 43, wherein said third material comprises polytetra-fluoroethlene.

45. The tubing assembly of claim 43, wherein said tubing assembly further comprises anti-slip rings disposed around said outer layer.

46. The tubing assembly of claim 35, wherein said outer layer further comprises a third material, wherein the exterior surface of said outer layer is coated with said third material and said coated exterior surface of said outer layer has a roughness peak count greater than about 45 peaks per cm.

47. The tubing assembly of claim 35, wherein said roughness peak count is between about 45 peaks per cm and about 100 peaks per cm.

48. The tubing assembly of claim 43, wherein said third material is polytetra-fluoroethlene.

49. The tubing assembly of claim 46, wherein said tubing assembly further comprises anti-slip rings disposed around said outer layer.

50. The tubing assembly of claim 35, wherein said second material comprises a polymer or a rubber material.

51. The tubing assembly of claim 35, wherein said second material comprises at least one material selected from the group consisting of Neoprene and chlorinated Neoprene.

52. The tubing assembly of claim 35, wherein said first material comprises stainless steel.

53. The tubing assembly of claim 35, wherein said at least one insulation chamber further comprises at least one first coiled element disposed within said at least one insulation chamber.

54. The tubing assembly of claim 35, wherein said at least one first coiled element is a spring.

55. The tubing assembly of claim 49, wherein said first acoustic chamber comprises at least one second coiled element disposed within said first acoustic chamber.

56. The tubing assembly of claim 35, wherein said at least one insulation chamber further comprises at least one gas element disposed within said at least one insulation chamber.

57. The tubing assembly of claim 35, wherein said at least one insulation chamber further comprises at least one liquid substance disposed within said at least one insulation chamber.

58. The tubing assembly of claim 35, wherein said at least one insulation chamber further comprises at least one displaceable solid disposed within said at least one insulation chamber.

59. The tubing assembly of claim 58, wherein said displaceable solid is foam.

60. The tubing assembly of claim 35, wherein said insulation chamber comprises at least one insulation layer disposed within said insulation chamber.

61. The tubing assembly of claim 60, wherein said at least one insulation layer substantially fills said insulation chamber.

62. A stethoscope comprising:

a head assembly;

an ear piece assembly; and a tubing assembly having a first end connected to said head assembly and a second end connected to said ear piece assembly, wherein an exterior surface of an outer layer of said tubing assembly has a roughness peak count greater than about 45 peaks per cm.

* * * * *